US005643494A

United States Patent [19]
Rittner et al.

[11] Patent Number: 5,643,494
[45] Date of Patent: Jul. 1, 1997

[54] PROCESS FOR THE PREPARATION OF AROMATIC HYDROXY CARBOXYLIC ACIDS

[75] Inventors: Siegbert Rittner, Mörfelden; Hans-Martin Rüffer, Hofheim; Jörg Schmid, Eppstein; Thomas Wisser, Limburg, all of Germany

[73] Assignee: Hoechst Aktiengesellschaft, Frankfurt, Germany

[21] Appl. No.: 456,499

[22] Filed: Jun. 1, 1995

Related U.S. Application Data

[62] Division of Ser. No. 245,960, May 19, 1994.

[30] Foreign Application Priority Data

May 21, 1993 [DE] Germany .................... 43 16 937.6

[51] Int. Cl.[6] ............................................. C09K 3/00
[52] U.S. Cl. ............................ 252/182.31; 562/424
[58] Field of Search ............................... 252/182.31

[56] References Cited

U.S. PATENT DOCUMENTS 3,655,744  4/1972  Yasuhara et al. .
4,966,992  10/1990  Ueno et al. .

FOREIGN PATENT DOCUMENTS

| 0053824 | 6/1982 | European Pat. Off. . |
| 0254596 | 1/1988 | European Pat. Off. . |
| 0081753 | 6/1988 | European Pat. Off. . |
| 0327221 | 8/1989 | European Pat. Off. . |
| 45-5532 | 2/1970 | Japan . |
| 1189385 | 4/1970 | United Kingdom . |
| WO81/02573 | 9/1981 | WIPO . |
| WO91/11422 | 8/1991 | WIPO . |

OTHER PUBLICATIONS

Patent Abstracts of Japan, vol. 6, No. 223 (C-133) (1101), Nov. 9, 1982.

Primary Examiner—Paul J. Killos
Attorney, Agent, or Firm—Curtis, Morris & Safford, P.C.

[57] ABSTRACT

A process for the preparation of aromatic hydroxy carboxylic acids by reacting alkali metal phenolates or alkali metal naphtholates with alkali metal carbonates and carbon monoxide, with subsequent acidification, wherein the solid starting materials—alkali metal carbonate and/or alkali metal phenolate or naphtholate—are metered into the reaction mixture in the form of one or more dispersions in an inert organic liquid.

The process according to the invention enables the preparation of aromatic hydroxy carboxylic acids in good yields and with high chemical selectivity. Additional measures for increasing the selectivity, as described for example for the Kolbe-Schmitt reaction in EP-A 0 053 824, EP-A 0 081 753 and EP-A 0 254 596, and for the reaction with CO and carbonate in, for example, WO 91/11422, are unnecessary.

20 Claims, 1 Drawing Sheet

NOH: 2-NAPHTHOL
KOH: POTASH LYE (50%)
NOK: KALIUMNAPHTHOLATE
DISP: DISPERSION
2,6-HNA: 2-HYDROXYNAPHTHALENE 6-CARBOXYLIC ACID

PROCESS FOR THE PREPARATION OF AROMATIC HYDROXY CARBOXYLIC ACIDS

This application is a division of application Ser. No. 08/245,960, filed on May 19, 1994.

BACKGROUND OF THE INVENTION

1. Field of Invention

The invention relates to a process for the preparation of aromatic hydroxy carboxylic acids or salts thereof by reacting a corresponding alkali metal phenolate or naphtholate with carbon monoxide and an alkali metal carbonate.

2. Description of the Related Art

Aromatic hydroxy carboxylic acids such as 2-hydroxynaphthalene-6-carboxylic acid are important intermediates, for example, in the production of dyes, polyesters, textile assistants and pharmaceuticals (see, for example, EP-A 0 292 955 and U.S. Pat. No. 4,393,191).

In industry, compounds of this kind are often prepared by the Kolbe-Schmitt reaction, i.e. by reacting a corresponding alkali metal phenolate or naphtholate with carbon dioxide (see e.g. EP-A 0 327 221 or U.S. Pat. No. 4,966,992). However, there is still room for improvement in the yields of these processes.

An alternative process for the preparation of aromatic hydroxy carboxylic acids is described in GB 1 155 776 (≙ U.S. Pat. No. 3,655,744). In this process specific aromatic alkali metal phenolates or alkaline earth metal phenolates or naphtholates are reacted with alkali metal or alkaline earth metal carbonates, carboxylates or dicarboxylates in the presence of carbon monoxide. The yields and, in particular, the selectivities of the process are likewise not adequate for all areas.

It was therefore desirable to improve the process described in the British patent application in respect of the yields and the selectivity of the reaction. It was also desirable to design the process in such a way that it can be carried out continuously in a simple manner.

Although GB 1 155 776 mentions the possibilities of a continuous reaction régime, the addition of solvents and the infeed and takeoff of solids as a suspension, it does not give concrete examples.

SUMMARY OF THE INVENTION

Surprisingly it has now been found that alkali metal phenolates and naphtholates and/or alkali metal carbonates form stable, flowable and pumpable dispersions with inert organic liquids at room temperature. It has been shown that, by reacting the solid starting materials in the form of such dispersions, the selectivity of the reaction can be increased considerably, especially if the addition to the reaction mixture is prolonged over the entire course of the reaction.

The invention therefore relates to a process for the preparation of aromatic hydroxy carboxylic acids by reacting alkali metal phenolates or naphtholates with alkali metal carbonates and carbon monoxide with subsequent acidification, wherein the solid starting materials—alkali metal carbonate and phenolates or naphtholates—are introduced in batches or continuously into the reaction mixture in the form of a dispersion with an inert organic liquid.

DESCRIPTION OF THE PREFERRED EMBODIMENTS

Figure 1:
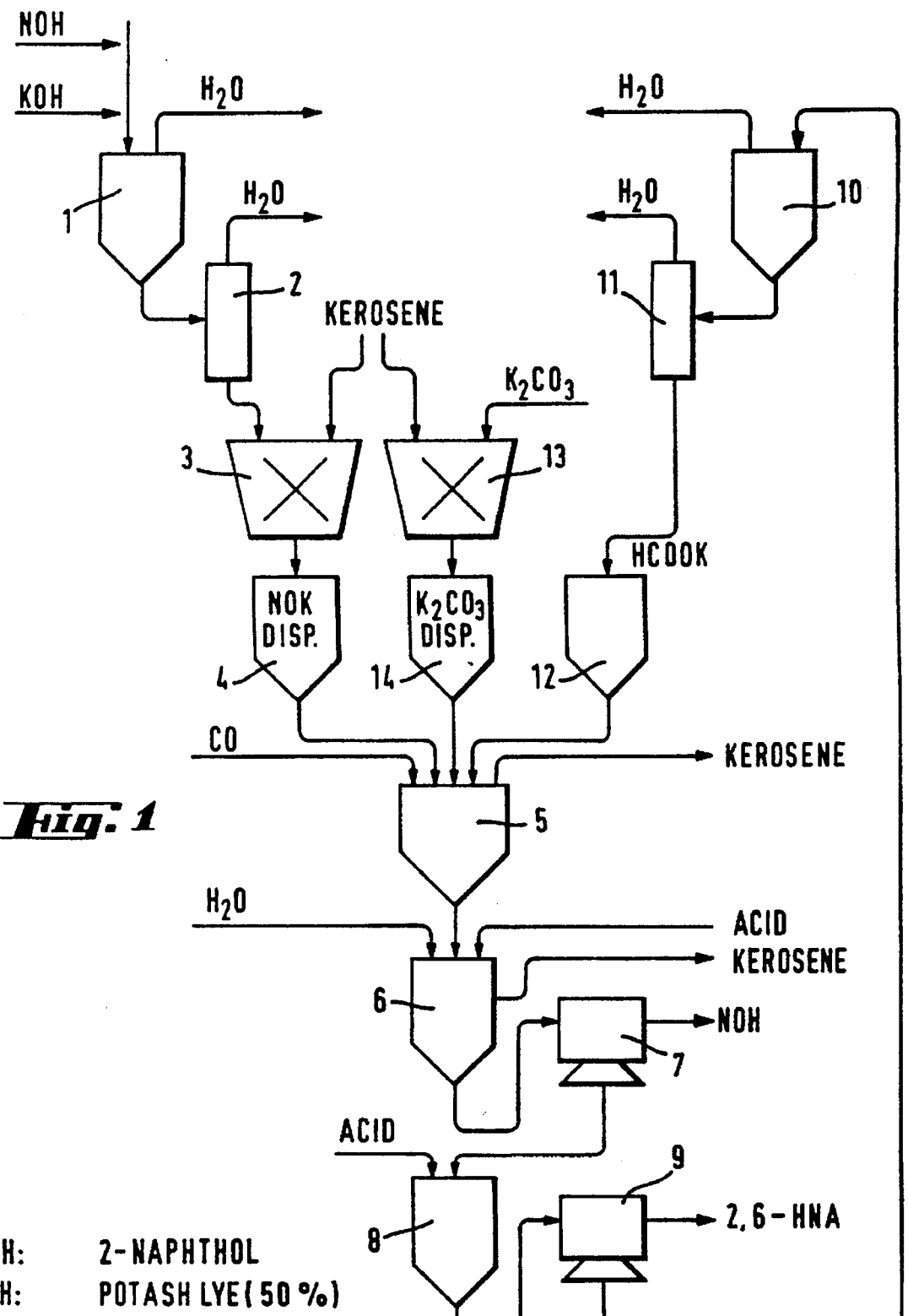
FIG. 1 illustrates an apparatus for carrying out the process according to one embodiment of the invention.

The process according to the invention enables the preparation of aromatic hydroxy carboxylic acids in good yields and with high chemical selectivity. Additional measures for increasing the selectivity, as described for example for the Kolbe-Schmitt reaction in EP-A 0 053 824, EP-A 0 081 753 and EP-A 0 254 596, and for the reaction with CO and carbonate in, for example, WO 91/11422, are unnecessary.

Thermally labile substances which are susceptible to oxidation, such as phenolates and naphtholates, can be metered in in batches or continuously at room temperature and do not, as previously, have to be metered in at high temperatures as a melt, while having to accept decomposition products.

Solids with high melting points, such as potassium carbonate, can also be metered in continuously.

Therefore the invention likewise relates to dispersions comprising an alkali metal carbonate and/or a phenolate or naphtholate and an inert organic liquid.

The phenolates or naphtholates preferably employed are compounds of the formula (I)

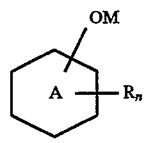

in which the symbols and indices have the following meanings:

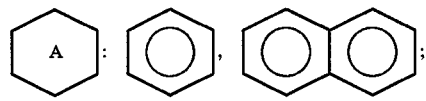

M: Li, Na, K;

R: each independently of one another OM, COOM, F, Cl, Br, I, NH$_2$, CF$_3$, an alkyl group having 1 to 6 carbon atoms, an alkoxy group having 1 to 6 carbon atoms;

n: 0, 1, 2, 3, 4.

Preferred meanings are:

M: Na, K;

R: —OM, —COOM, an alkyl group having 1 to 6 carbon atoms;

n: 0, 1, 2.

Particularly preferred meanings are:

M: K;

R: COOM, —CH$_3$;

n: 0.1.

Particularly preferred compounds of the formula (I) are sodium β-naphtholate and potassium β-naphtholate.

The alkali metal phenolates and napholates employed according to the invention can be prepared by reacting the corresponding phenols or naphthols with basic alkali metal compounds such as sodium hydroxide and potassium hydroxide.

Carbonates which can be employed in the process according to the invention are all alkali metal carbonates and hydrogen carbonates, i.e. Li$_2$CO$_3$, LiHCO$_3$, Na$_2$CO$_3$, NaHCO$_3$, K$_2$CO$_3$, KHCO$_3$, Rb$_2$CO$_3$, RbHCO$_3$, Cs$_2$CO$_3$ and CsHCO$_3$. It is preferred to employ Na$_2$CO$_3$ and K$_2$CO$_3$, especially K$_2$CO$_3$.

The carbonates used in accordance with the invention should preferably contain little moisture, especially less than 0.5% by weight of water.

Based on the phenolate or naphtolate employed, at least equivalent quantities of carbonate should be employed. In general the stoichiometric ratio of phenolate or naphtholate to carbonate is from 1:1 to 1:4, preferably from 1:1 to 1:3 and particularly preferably from 1:1 to 1:1.5.

The particle size of the solid starting materials employed (phenolate, naphtholate and carbonate) is preferably below 50 μm, particularly preferably below 10 μm and especially between 0.1 and 10 μm.

Suitable grinding apparatus for the solid starting materials comprises all machines for comminution, for example mills which are able to comminute brittle solids to particle sizes of this kind. Particularly good results are obtained by grinding the solids wet directly with the dispersant, for example in ball mills.

The dispersion media employed for the preparation of the dispersion according to the invention are substances or mixtures of substances which are inert under the reaction conditions, are liquid and are temperature-stable, such as aliphatic, alicyclic or aromatic hydrocarbons derived from petroleum distillation. Of particular suitability are light oil, heavy oil, preferably kerosene, aromatics and alkyl derivatives thereof, such as toluene, xylene, isopropyl- or diisopropylnaphthalene, biphenyl, alkyl-biphenyls, triphenyl and alkyltriphenyls, and aliphatic and aromatic ether compounds and alkyl derivatives thereof, such as diphenyl ether, anisole, dicyclohexyl ether, and mixtures of these. The dispersion media do not interfere with the reaction and can be removed from the reactor by distillation or separated off, following the reaction, by allowing the reaction mixture to settle or subjecting it to distillation. They have the advantage that, after the removal of any dissolved or entrained components, such as β-naphthol or water, they can be used again for the production of fresh dispersions.

The metered addition of the phenolates or naphtholates and of the carbonate can take place in a combined dispersion or in dispersions of individual materials, the latter possibility opening up a wider scope for variation in the reaction régime.

For their introduction into the reaction mixture, suitable metering devices are all those which are able to convey the suspensions or pastes counter to the pressure in the reactor, such as piston pumps, membrane pumps, extruders and eccentric screw pumps.

The composition by weight of the dispersion can lie within broad limits, and depends on whether it is to be conveyed as an easily fluid medium or in a pasty form. A suitable proportion by weight of alkali metal phenolate or naphtholate is from 5 to 70% by weight, preferably from 25 to 60% by weight and in particular between 40 and 55% by weight, based on the mass of the dispersion. The limits within which potassium carbonate can be employed are from 5 to 65% by weight, preferably from 20 to 55% by weight and in particular from 25 to 40% by weight, based on the overall weight of the dispersion. With solids contents of less than 25% by weight, settling is sometimes observed, which can be prevented merely by moderate stirring or pumping.

The organic liquid dispersion media described can also be added to the reaction as additional solvents and diluents, preferably in quantities of from 10 to 300% by weight, particularly preferably from 50 to 150% by weight, based on the solid starting materials.

In analogy to the process described in EP-A 0 081 753, for separating off secondary products in the Kolbe-Schmitt synthesis of 2-hydroxynaphthalene-6-carboxylic acid, the dispersion medium and/or an additional diluent can also be used for separating off secondary products.

For some reactions it is advantageous, as described in WO 91/11422, to add to the reaction mixture potassium formate, which is present under the conventional reaction conditions as a clear, nonviscous melt. It acts as a solvent and diluent and is preferably employed in amounts of from 50 to 1000% by weight, particularly preferably from 100 to 300% by weight, based on the solid starting materials.

The process according to the invention is carried out in the presence of CO. The CO can be present as a gas atmosphere over the reaction mixture or can be injected onto or even directly into the mixture. To allow the reaction to progress to completion, at least stoichiometric quantities, based on the phenolate or naphtholate, of CO are required.

The process according to the invention is carried out at a pressure of from 1 to 150 bar, preferably from 5 to 100 bar and particularly preferably from 10 to 30 bar, the pressure referred to being that at the reaction temperature.

Technical-grade carbon monoxide can be used, i.e. small quantities of other gases such as $N_2$, $CH_4$, $CO_2$ and $H_2$ are not critical.

The reaction temperature can be varied within wide limits depending on the properties of the starting materials, products and solvents or dispersants. The reaction is in general carried out at temperatures of from 150° to 400° C., preferably from 150° to 350° C. and especially preferably from 200° to 350° C. The duration of the reaction is preferably between 1 and 40 hours.

Various forms of apparatus can be used in carrying out the process according to the invention for example, the reactor used may be a pressure vessel or header which is fitted with a stirring element which is efficient in terms of thorough mixing and CO gassing, this reactor being connected with a feed system for the dispersion. The dispersion can either be metered in in cycles, pumped in or injected, or metered in continuously.

In a preferred variant of the process according to the invention the phenolate or naphtholate, the carbonate and the dispersion medium are ground and the resulting dispersion is introduced continuously or in cycles into a preheated reactor charged with CO and, if desired, with solvent and carbonate. When the reaction is over the alkali metal salt formed is converted into the acid in a conventional manner and, if desired, is purified by known methods.

The process according to the invention can be carried out batchwise, semicontinuously or continuously.

FIG. 1 illustrates a possible variant apparatus for carrying out the process according to the invention.

Together with aqueous potassium hydroxide solution, 2-naphthol is dewatered in the evaporator (1) and freed from residual moisture in the drier (2). The potassium naphtholate melt formed is subsequently ground with kerosene in the mill (3) to give a dispersion, during which cooling is applied, and is stored in the tank (4). The potassium formate melt, which may have been recycled, after dewatering in the evaporator (10) and drier (11), is charged to the reactor (5) via the metering vessel (12). The suspensions of potassium naphtholate and potassium carbonate are fed in continuously under CO pressure (they are prepared by grinding with kerosene in the mill (13) and are stored in the tank (14)). After reaction has taken place the reaction melt is taken up in water in the stirring vessel (6), and the upper, kerosene phase is separated off after settling and adjusted to neutral using sulfuric acid. The precipitated 2-naphthol is separated off in the centrifuge (7). The acidification and precipitation of the 2-hydroxynaphthalene-6-carboxylic acid takes place analogously in (8) and (9).

The aromatic hydroxy carboxylic acids prepared by the process according to the invention are important intermediates in the production of polyesters, azo dyes and pharmaceuticals.

2-Hydroxynaphthalene-6-carboxylic acid in particular is not only a valuable building block in the synthesis of dyes, textile assistants and pharmaceuticals (see e.g. EP-A 0 292 955 A), but in particular is also an important monomer in the production of liquid crystal polymers having outstanding properties (see e.g. U.S. Pat. No. 4,393,191).

The examples which follow illustrate the invention described above. Parts and percentages are by weight unless stated otherwise. The relationship between parts by weight and parts by volume is that of the kilogram to the liter.

EXAMPLES

Example 1

A stainless steel pressure autoclave is charged with 100 parts of potassium formate and the melt is freed from residual moisture at 230° C., with stirring and in vacuo. It is then heated to 280° C. and 50 bar of carbon monoxide are injected. Using a metering pump, a mixture of 20 parts of potassium naphtholate with 25 parts of potassium carbonate are metered in as a suspension in kerosene over a period of 5 hours. Some of this kerosene is removed from the reaction vessel by distillation under reduced pressure, and is condensed and expelled. After it has been cooled, the reaction mixture is taken up in water, and the upper, kerosene phase is separated off after settling. The reaction mixture is acidified with sulfuric acid to a pH of 7 and then the unreacted β-naphtholate precipitates and is separated off. On further acidification to pH 4, first the 2-hydroxynaphthalene-6-carboxylic acid precipitates, and finally at pH 1 the other acids do likewise. The reaction mixture is worked up to give 2-hydroxynaphthalene-6-carboxylic acid in a yield of 72% based on the potassium naphtholate employed. Secondary products are 8% of unreacted γ-naphthol, 4% of 2-hydroxynaphthalene-3-carboxylic acid and 12% of 2-hydroxynaphthalene-3,6-dicarboxylic acid.

Example 2

A stainless steel pressure autoclave is charged with 50 parts of kerosene and 10 parts of potassium formate and heated to 280° C. 50 bar of carbon monoxide are then injected. Using a metering pump, a mixture comprising 50 parts of potassium naphtholate and 38 parts of potassium carbonate is metered into the reactor as a suspension in kerosene over the course of 5 hours. Some of this kerosene is removed from the reaction vessel by distillation under reduced pressure, and is condensed and expelled. The reaction mixture is worked up conventionally to give 2-hydroxynaphthalene-6-carboxylic acid in a yield of 67% based on the potassium naphtholate employed. Secondary products are 15% of unreacted β-naphthol, 4% of 2-hydroxynaphthalene-3-carboxylic acid and 9% of 2-hydroxynaphthalene-3,6-dicarboxylic acid.

We claim:

1. A mixture comprising:
   a) from 5 to 50% by weight of alkali metal carbonate;
   b) from 5 to 70% by weight of an alkali metal phenolate or alkali metal naphtholate; and
   c) from 5 to 95% by weight of an aliphatic or aromatic hydrocarbon or an aliphatic or aromatic ether, or a mixture of at least two of these compounds.

2. A mixture as claimed in claim 1, wherein the alkali metal carbonate and phenolate or naphtholate have an average particle size of less than 50 μm.

3. The mixture as claimed in claim 1, wherein said alkali metal carbonates are selected from the group consisting of Li$_2$CO$_3$, LiHCO$_3$, Na$_2$CO$_3$, NaHCO$_3$, K$_2$CO$_3$, KHCO$_3$, Rb$_2$CO$_3$, RbHCO$_3$, Cs$_2$CO$_3$ and CsHCO$_3$.

4. The mixture as claimed in claim 1, wherein said alkali metal carbonates are selected from the group consisting of Na$_2$CO$_3$ and K$_2$CO$_3$.

5. The mixture as claimed in claim 1, wherein said alkali metal carbonates comprise less than 0.5% by weight water.

6. The mixture as claimed in claim 1, wherein said solid starting materials have a stoichiometric ratio of phenolate or naphtholate to carbonate ranging from 1:1 to 1:4.

7. The mixture as claimed in claim 1, wherein the mixture has an average particle size of less than 10 microns.

8. The mixture as claimed in claim 1, wherein the phenolate or naphtholate employed is a compound of the formula (I)

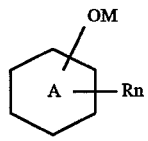

in which the symbols and indices have the following meanings:

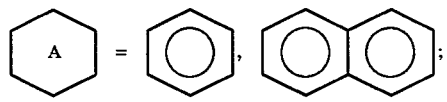

M: Li, Na, K;

R: each independently of one another OM, COOM, F, Cl, Br, I, NH$_2$, CF$_3$, an alkyl group having 1 to 6 carbon atoms, an alkoxy group having 1 to 6 carbon atoms, and n: 0, 1, 2, 3, 4.

9. The mixture as claimed in claim 1, wherein the alkali metal naphtholate employed is potassium β-naphtholate.

10. A mixture comprising:
    a) from 5 to 50% by weight of alkali metal carbonate; or
    b) from 5 to 70% by weight of an alkali metal phenolate or alkali metal naphtholate; and
    c) from 5 to 95% by weight of an aliphatic or aromatic hydrocarbon or an aliphatic or aromatic ether, or a mixture of at least two of these compounds.

11. A mixture as claimed in claim 10, wherein the alkali metal carbonate or phenolate or naphtholate have an average particle size of less than 50 μm.

12. The mixture as claimed in claim 10, wherein said alkali metal carbonates are selected from the group consisting of Li$_2$CO$_3$, LiHCO$_3$, Na$_2$CO$_3$, NaHCO$_3$, K$_2$CO$_3$, KHCO$_3$, Rb$_2$CO$_3$, RbHCO$_3$, Cs$_2$CO$_3$ and CsHCO$_3$.

13. The mixture as claimed in claim 10, wherein said alkali metal carbonates are selected from the group consisting of Na$_2$CO$_3$ and K$_2$CO$_3$.

14. The mixture as claimed in claim 10, wherein said alkali metal carbonate is K$_2$CO$_3$.

15. The mixture as claimed in claim 10, wherein said alkali metal carbonates comprise less than 0.5% by weight water.

16. The mixture as claimed in claim 10, wherein the mixture has an average particle size of less than 10 microns.

17. The mixture as claimed in claim 10, wherein the phenolate or naphtholate employed is a compound of the formula (I)

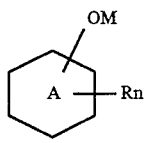

in which the symbols and indices have the following meanings:

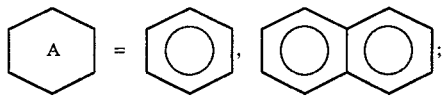

M: Li, Na, K;

R: each independently of one another OM, COOM, F, Cl, Br, I, $NH_2$, $CF_3$, an alkyl group having 1 to 6 carbon atoms, an alkoxy group having 1 to 6 carbon atoms, and n: 0, 1, 2, 3, 4.

18. The mixture as claimed in claim 10, wherein the alkali metal naphtholate employed is potassium β-naphtholate.

19. The mixture as claimed in claim 10, wherein the dispersion comprises from 5 to 50% by weight, based on the overall dispersion, of alkali metal carbonate.

20. The mixture as claimed in claim 10, wherein the dispersion comprises from 5 to 70% by weight, based on the overall dispersion, of alkali metal phenolate or alkali metal naphtholate.

* * * * *